(12) United States Patent
Vija

(10) Patent No.: US 7,467,008 B2
(45) Date of Patent: Dec. 16, 2008

(54) ECTOGRAPHY MULTIMODALITY IMAGING SYSTEM FOR DIAGNOSIS AND TREATMENT

(75) Inventor: A Hans Vija, Evanston, IL (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 254 days.

(21) Appl. No.: 11/526,480

(22) Filed: Sep. 25, 2006

(65) Prior Publication Data

US 2007/0078329 A1    Apr. 5, 2007

Related U.S. Application Data

(60) Provisional application No. 60/722,509, filed on Sep. 30, 2005.

(51) Int. Cl.
*A61B 5/00* (2006.01)

(52) U.S. Cl. .................. 600/436; 250/363.1; 378/5; 600/407; 600/411

(58) Field of Classification Search .............. 600/407, 600/415, 425, 427, 417, 411, 436, 431; 378/19, 378/92; 250/581, 582, 496.1, 515, 370.01, 250/363.04, 363.03; 5/603, 610
See application file for complete search history.

(56) References Cited

U.S. PATENT DOCUMENTS

| 5,864,146 A * | 1/1999 | Karellas ..................... 250/581 |
| 6,982,430 B1 * | 1/2006 | Moscaritolo et al. ...... 250/496.1 |
| 2003/0128801 A1 * | 7/2003 | Eisenberg et al. ............. 378/19 |
| 2006/0291628 A1 * | 12/2006 | Clayton ...................... 378/143 |

* cited by examiner

*Primary Examiner*—Eric F Winakur
*Assistant Examiner*—Lawrence N Laryea
(74) *Attorney, Agent, or Firm*—Peter L. Kendall

(57) ABSTRACT

A system and method of integrating a nuclear medicine imaging device such as a gamma camera with a patient handling system where the nuclear medicine imaging system does not prevent full access to the patient and does not interfere with the field of view of accompanying modalities accommodated by use of the patient handling system.

26 Claims, 2 Drawing Sheets ic/ ECTOGRAPHY MULTIMODALITY IMAGING SYSTEM FOR DIAGNOSIS AND TREATMENT

CROSS-REFERENCE TO RELATED APPLICATION AND CLAIM FOR PRIORITY

This application claims priority under 35 U.S.C. § 119(e) from provisional application Ser. No. 60/722,509 filed Sep. 30, 2005.

BACKGROUND OF THE INVENTION

1. Field of the Invention

The present invention generally relates to nuclear medicine, and systems for obtaining nuclear medicine images of a patient's body organs of interest in conjunction with other detection systems. In particular, the present invention relates to a system and method for the tomographic and limited angle tomographic emission acquisition while remaining outside the field of view of accompanying scanning devices for multiple modality imaging.

2. Description of the Background Art

In the field of medicine there has been development of various imaging and scanning devices to aid in the treatment and diagnoses of patients. Many of these devices require considerable amounts of space, and furthermore, if testing requires use of different imaging devices, substantial amounts of time in addition to space is required to conduct the separate scans. In many cases such as in operating rooms or RT rooms, space is at a premium. Moreover, many of the devices have different clinical strengths, where some are effective at indicating functional aspects of the target, such as blood flow in the brain, others are effective at indicating structural aspects, such as bone structure or organ anatomy. Therefore, different imaging devices have been combined to improve the efficiency of hospitals and other medical facilities in the effective use of time and space, and also to enable multiple modality imaging to combine the different strengths of various imaging devices and offset their weaknesses as standalone systems.

Examples of scanning devices which can be used as standalone systems or integrated for dual modality scanning are Single Photon Emitted Computerized tomography (SPECT) and Computed Axial Tomography (CT), as well as positron emission tomography (PET), as well as Magnetic Resonance Imaging (MRI), as well as treatment systems such as Intensity-Modulated Radiation Therapy (IMRT). Such systems can be combined with each other in any number of dual modality combinations for example CT/SPECT, CT/MRI, PET/MRI, and CT/IMRT. Examples of such combined systems are shown in U.S. Pat. Nos. 7,075,087, 6,631,284, and 6,490,476, each incorporated by reference herein in its entirety.

One of the difficulties in integrating such systems for multiple modalities is their inherent space and operating requirements. CT/MRI/PET systems require a particular field of view (FOV) free of impediments that may block the view of the detectors used by the system. Therefore the operation of one system cannot be such that it interferes with the FOV of another system, thereby preventing it from carrying out its scanning activity.

Currently, in many of the ectography and tomography techniques, the patient is scanned by directing the detection devices on some orbit either fully or partially fulfilling the well-known Orlov conditions for tomography. Often, with such systems, the patient bed is used to move the patient, while the detection systems, with a gantry, follow some specified path about the patient in order to fulfill conditions to allow for an appropriate dataset. Such operational requirements prevent simultaneous scanning and unencumbered access to the patient, thereby preventing appropriate care of the patient and effective use of technology and medical facility resources.

Furthermore, current art concerning triple modality systems only envisage aligning the modalities along the tomographic axis (the longitudinal axis of the patient), which make such devices too large. However, certain aspects of SPECT imaging systems have been developed which may lend themselves to use of triple modalities and concurrent full patient access.

In particular, the SPECT system is a nuclear imaging technique wherein radiopharmaceuticals are introduced into the body, either by injection or ingestion, and are attracted to specific organs, bones or tissues of interest. Such radiopharmaceuticals produce gamma photon emissions that emanate from the body and one or more detectors are used to detect the emitted gamma photons. Collimators are placed in front of the detectors to permit only those beams of radiation emanating along a particular path to pass through to be detected by the detector, so that no scattered or environmental background photons are detected. The information is then processed and used to create tomographic images of the patient. Many different schemes and methods of detection have been employed, from using differently shaped collimators to different placement and rotations of the detectors to achieve a full sampling of the target patient.

What is needed therefore, is a method or device which provides for the integration of SPECT with other modalities without impeding the FOV of the separate accompanying scanning devices and providing full access to the patient.

SUMMARY OF THE INVENTION

A system and method for scanning a patient which allows full access to a target subject, or patient and does not interfere with the FOV of accompanying modalities is described herein. Such a system enables the efficient use of time and space in hospitals with regard to imaging devices and similar devices. Such a system also enables the use of dual or additionally triple modalities for treatments and scanning in conjunction with SPECT scanning.

The system and method is therefore directed toward the integration of a SPECT scanning device with a patient handling system without the use of a gantry. By integrating the scanning device with the patient handling system less space is taken up, and combination with other modalities is facilitated, while also enabling full access to the patient by medical personnel during scanning.

DETAILED DESCRIPTION OF THE PREFERRED EMBODIMENTS

Figure 1:
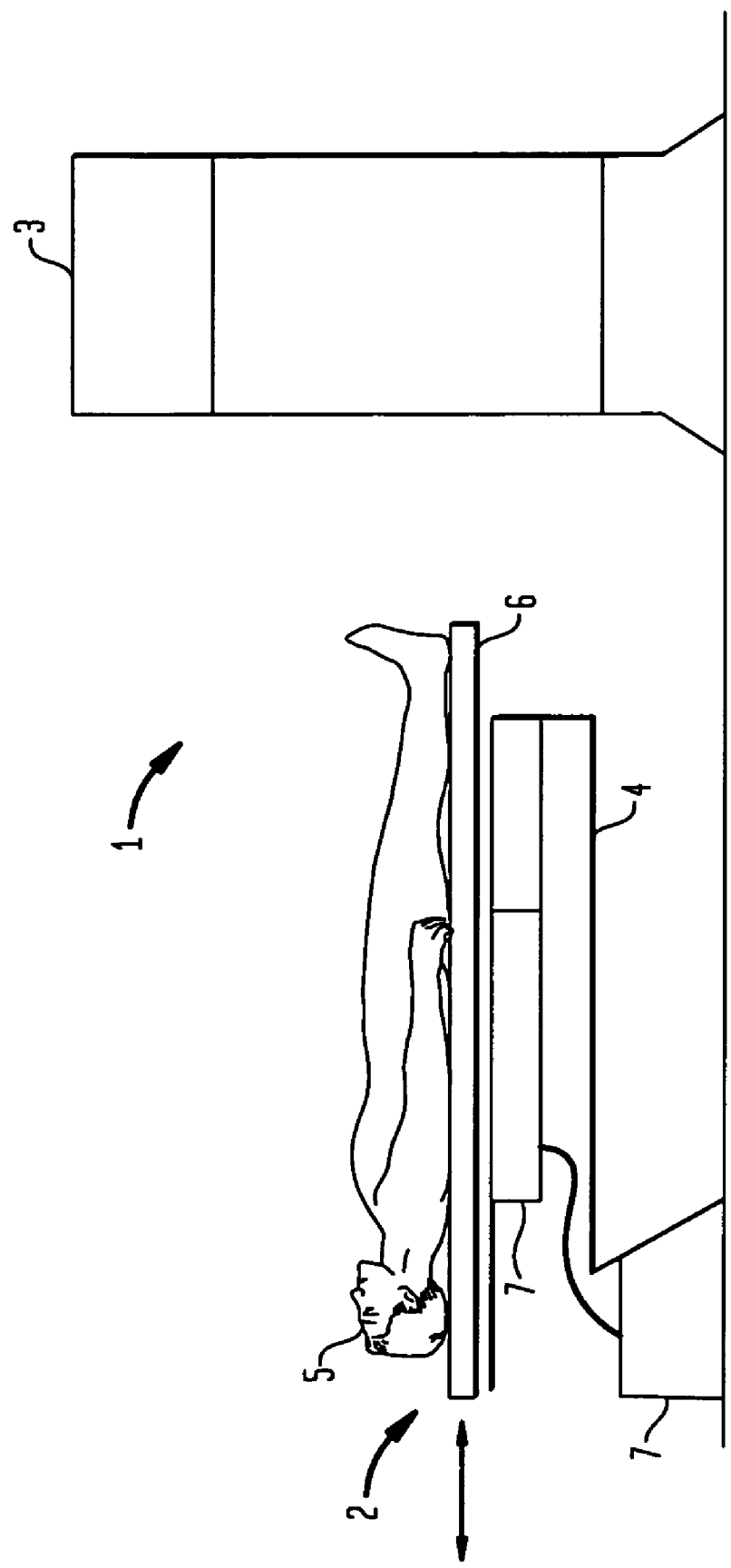
FIG. 1 is a side view of a SPECT imaging system in combination with one or more other modalities, in accordance with the present invention.

The multimodality imaging system 1 is illustrated in FIG. 1. As can be seen in the figure, the system is a nuclear medicine imaging device 4, such as a gamma camera, which is integrated with a patient handling system (PHS) 2. Patient handling systems are already known in the art. Generally such systems provide for the comfortable support of a patient 5 as the patient is undergoing analysis or treatment by imaging devices or similar medical devices. The patient handling system is usually adapted to move the patient or translate the patient in the appropriate manner for the medical device to conduct the imaging analysis or treatment. The patient handling system can be as simple as a bed. In one embodiment, the patient handling system has at least a patient bed 6 and a support 7, with the support in some embodiments allowing for moving the bed, and translating the patient. In some embodiments, the Siemens Symbia patient handling system could be used for integration with the imaging device 4.

The accompanying imaging device 3 can be any device that performs functional or structural imaging of a target subject such as a patient, or other target object. The imaging device 4 is arranged such that it can scan a patient 5 who is resting on the bed 6 of the PHS 2 without impeding access to said patient 5. In some embodiments, the patient handling system has an open area beneath the patient bed 6. The open area can exist under the bed 6 before translation of the patient takes place or as the patient is translated. The nuclear medicine imaging device 4 can be placed beneath the bed 6 in the open area, facing in a direction enabling scanning of the patient 5. In further embodiments the nuclear medicine imaging device can be on a wheeled support, which can be easily moved beneath the bed 6. In even further embodiments, the Symbia PHS could be used if the internal collimator storage is replaced by a detection system. The support 7 in the patient handling system can vary, such that it can take up a large portion of the space under the bed or very little. A nuclear medicine imaging device could be placed beneath bed 6, in the support 7 of the patient handling system as displayed in FIG. 2 if the support takes up a large area. This support area may otherwise be for storage, support, or any other function.

The nuclear medicine imaging device must be arranged such that it is able to scan a target on the bed 6 while not interfering with the FOV of one or more other accompanying imaging devices 3, or anatomical modalities. The imaging device 4 must also be arranged such that there is full access to the patient during the scanning procedure. Therefore the nuclear medicine device will not have a moving gantry, or require support that prevents access to the patient or interferes with the FOV of accompanying scanning devices 3. Full access is that which allows medical personnel to attend to the patient without being impeded by any structure associated with the nuclear medicine imaging system, such as a gantry or other parts.

The other scanning devices 3 may be, but are not limited to, a CT, PET, or MRI, or any combination of two modalities such as PET/CT, PET/MRI or CT/IMRT as non-limiting examples. This allows scanning of the patient in combination with up to two additional modalities. Functional and structural as well as other modalities can then be combined to produce a more complete image of the target subject. Therefore, in combination with the non-interfering nuclear medicine imaging device, there can be a total of up to three modalities.

In some embodiments, the nuclear medicine imaging of the patient 5 will occur by movement or translation of the patient. As the patient is moving toward the accompanying anatomical modalities 3, the nuclear medicine imaging of the patient can take place. After nuclear medical scanning, or as the nuclear medical scanning takes place, the patient will pass through the FOV of the other imaging devices 3 for collection of their target data sets. In other embodiments, the patient will remain stationary as the nuclear medical scanning occurs.

Figure 2:
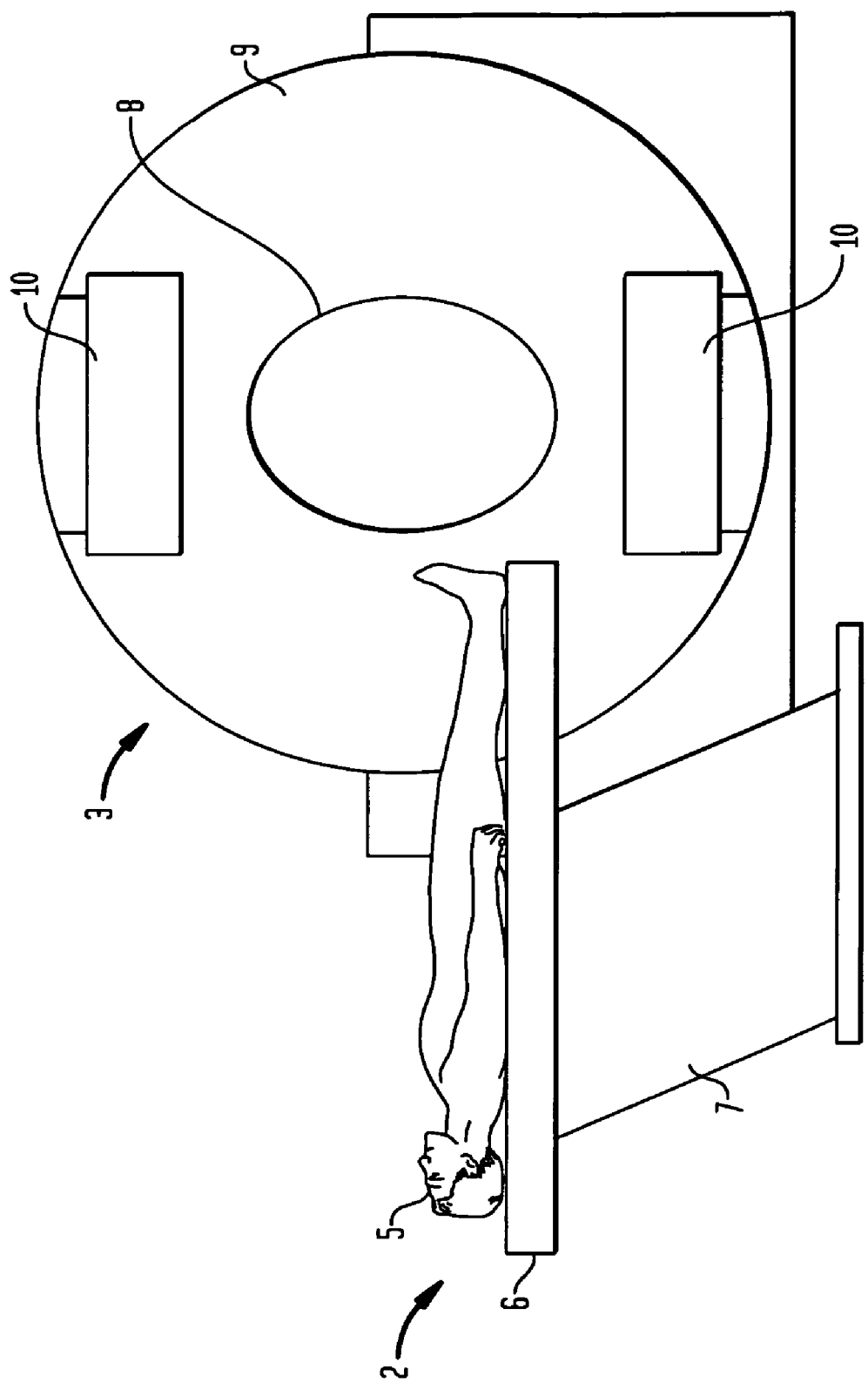
FIG. 2 is a perspective view of a SPECT imaging system in combination with one or more other modalities, in accordance with the present invention.

As seen in an embodiment in FIG. 2, the accompanying scanning devices 3 are generally aligned along the longitudinal axis of the patient or patient bed. In FIG. 2 there can be seen a large gantry 9 with an aperture 8 for receiving a patient, such as is provided by a CT scanner. As can be seen, the patient handling system is arranged such that the bed carrying the patient will move such that the patient will pass through the FOV in the aperture 8 of scanning device 3. Some modalities are shaped differently, and so there may be a circular type scanning device, or any other shape according to the needs of the particular device. Further modalities can be added to the first and aligned one after the other which can be of any shape that is required by the particular medical device. Such device can be another circular scanning device or can have separate scanning parts to view from above and below such as separate detector heads/sources 10, or from either side of the patient, or comprise any other shape required by the device and circumstances.

Regarding the nuclear medicine imaging device, generally any type of collimator and detecting device can be used which enables tomography or limited angle tomography of the patient or target object which does not interfere with the FOV of the other accompanying devices 3 and provides full access to the patient during imaging. However, there are already nuclear medicine systems in existence which could immediately be integrated with the patient handling system 2. In some embodiments the patient handling system could be integrated with a scanning device having a rotating acceptance angle collimator. Such a collimator can remain stationary during scanning while the patient is translated. The collimator is such that the aperture passageways in the collimator are arranged so that the angle of view of each row varies with respect to a radiation source thus allowing scanning of the patient from different angles with respect to the patient. This type of collimator is therefore capable of obtaining a substantially complete angular sampling in as little as a single pass of a camera along the patient, using only one-dimensional relative motion between the camera and the patient. Such a collimator allows more complete sampling as the patient is moved toward the other modalities despite scanning from one dimension. Furthermore, use of such a collimator does not require a gantry, but in combination with a camera can be placed under an existing bed or pallet or integrated in other ways with the PHS to properly scan the patient without entering the FOV of the other accompanying scanning devices 3.

Additionally, a rotating slat collimator can be used for integration with the PHS while facilitating patient treatment or scanning in combination with accompanying modalities. With such a collimator, the patient will be kept stationary as the scanning takes place. The rotating slat collimator is used in combination with a gamma camera having a scintillation detector formed of a stack of scintillation bar detectors. The slat collimator collimates each of the bar detectors to receive gamma photons in only a single dimension. The scintillation bar detectors and collimator can be rotated to obtain event data from the target subject at a number of azimuth angles of the rotating device for reconstruction of the tomographic image. Such a nuclear medicine imaging device can be mounted under the bed or pallet, and also in the support of the patient handling system. Additionally, a parallel hole collimator can be used. Any other nuclear medicine imaging systems or systems performing functional imaging can be used which can be integrated with the patient handling system enabling full access to the patient without interfering with the FOV of accompanying different modality imaging devices.

Such devices will likely provide scanning from one direction because in many embodiments the device will be beneath the patient. Therefore, scanning devices which are able to provide more complete tomographic image while scanning from one dimension are preferred. Embodiments of the present invention encompass all detection mechanisms using either conventional crystal/photomultiplier combinations or solid state technologies.

Additional embodiments of the current invention will include shielding for the detection device integrated with the patient handling system. The imaging device and electronics can be enclosed in a protective sealed casing in such a way as to protect the camera. For example lead should be used if one of the accompanying devices uses radiation such as CT, SPECT or PET, or copper should be used with MRI. A low attenuation, low Z material can be used to mechanically protect the collimator of the device. A movable shield can be used which closes during the scanning of other modalities.

What is claimed is:

1. A multimodality imaging system comprising:
    an anatomical imaging device having a field of view (FOV);
    a Patient Handling System (PHS), wherein said PHS has a bed and a support for said bed, for positioning a patient to be imaged by said anatomical imaging device;
    a nuclear medicine imaging device, having a radiation detector and a collimator being integrated and movable with said PHS such that imaging of a patient on said bed can be conducted without said nuclear medicine imaging device interfering with the field of view of said anatomical imaging device.

2. The multimodality imaging system of claim 1, wherein said bed is movable in the longitudinal axis of the bed so that a target patient contained on said bed may be translated with respect to said anatomical imaging device.

3. The multimodality imaging system of claim 2, wherein the nuclear medicine imaging device is integrated with said PHS such that scanning of a target patient can be conducted without impeding full access to the target patient by medical personnel during scanning.

4. The multimodality imaging system of claim 3, wherein the target patient is scanned by the nuclear medicine device and thereafter translated into the FOV of one or more accompanying imaging modalities for scanning or treatment by said modalities.

5. The multimodality imaging system of claim 3, wherein the nuclear medicine imaging device is enclosed in a protective sealed casing.

6. The multimodality imaging system of claim 5, wherein said casing is a movable shield, and comprised of low attenuation, low Z material; and wherein said movable shield closes during use of accompanying modalities.

7. The multimodality imaging system of claim 5, wherein the casing is constructed of lead or copper.

8. The multimodality imaging system of claim 3, wherein the target subject is translated into the FOV of one or more other accompanying modalities after target subject is scanned by said nuclear medicine imaging device.

9. The multimodality imaging system of claim 2, wherein the target patient is scanned by the nuclear medicine imaging device while the target patient is translated on the bed for imaging by said anatomical imaging device.

10. The multimodality imaging system of claim 1, wherein the collimator is a rotating acceptance angle collimator.

11. The multimodality imaging system of claim 1, wherein the collimator is a rotating slat collimator.

12. The multimodality imaging system of claim 1, wherein the nuclear medicine imaging device is located beneath the bed.

13. The multimodality imaging system of claim 1, wherein a substantial amount of the nuclear medicine imaging device is located beneath the bed.

14. The multimodality imaging system of claim 1, wherein the nuclear medicine imaging device is not fixed or attached to a gantry.

15. The multimodality imaging system of claim 1, wherein the target patient is scanned while the target subject is held stationary on the bed.

16. The multimodality imaging system of claim 1, wherein said anatomical imaging device contains at least two accompanying modalities.

17. The multimodality imaging system of claim 16, wherein said accompanying modalities are selected from the group of CT, MRI, PET, IMRT, or any combination of two of such modalities, thereby enabling a dual or triple modality system.

18. The multimodality imaging system of claim 1, wherein said nuclear medicine scanning device is a planar gamma camera.

19. A method for multimodality scanning of a patient comprising:
    integrating a nuclear medicine scanning device with a Patient Handling System (PHS) that is used to position a patient for imaging by an accompanying imaging modality having a field of view (FOV), such that the scanning device is movable with the PHS and does not interfere with the field of view of said accompanying imaging modality, wherein said PHS has a bed and a support for said bed, and wherein the nuclear medicine scanning device has a detector and a collimator; and
    scanning the patient by the nuclear medicine scanning device such that the scanning device does not prevent full access to the patient during scanning.

20. A method for multimodality scanning as in claim 19 wherein the nuclear medicine scanning device is outside the field of view of any accompanying modalities.

21. A method for multimodality scanning as in claim 20 wherein said accompanying modality is a choice of CT, MRI, PET, IMRT and a combination thereof, thereby enabling a dual or triple modality system.

22. A method for multimodality scanning as in claim 21 further comprising translating the patient into the FOV of any accompanying modalities.

23. A method for multimodality scanning as in claim 22 wherein images from the scanning of the nuclear medicine device and scanning of the accompanying modalities are combined for a multimodality image of the patient.

24. A method for multimodality scanning as in claim 19 wherein the collimator is a rotating acceptance angle collimator.

25. A method for multimodality scanning as in claim 19 wherein the collimator is a rotating slat collimator.

26. A method for multimodality scanning as in claim 19 wherein the nuclear medicine device is located beneath the bed.

* * * * *